United States Patent [19]

Herve Dallemagne

[11] Patent Number: 5,456,695

[45] Date of Patent: Oct. 10, 1995

[54] MULTI-TOOL SURGICAL APPARATUS

[75] Inventor: Bernard G. Herve Dallemagne, Angleur, Belgium

[73] Assignee: United States Surgical Corporation, Norwalk, Conn.

[21] Appl. No.: 142,153

[22] Filed: Oct. 25, 1993

[51] Int. Cl.⁶ ..................................................... A61B 17/00
[52] U.S. Cl. ........................................ 606/207; 606/198
[58] Field of Search ................................. 606/191, 198, 606/205–210; 128/750–755

[56] References Cited

U.S. PATENT DOCUMENTS

| | | |
|---|---|---|
| 5,147,373 | 9/1992 | Ferzli . |
| 5,147,378 | 9/1992 | Markham . |
| 5,174,300 | 12/1992 | Bales et al. . |
| 5,195,505 | 3/1993 | Josefsen . |
| 5,199,419 | 4/1993 | Remiszewski et al. . |
| 5,201,759 | 4/1993 | Ferzli ..................................... 606/207 |
| 5,261,917 | 11/1993 | Hasson et al. . |
| 5,290,299 | 3/1994 | Fain et al. ............................. 606/207 |

OTHER PUBLICATIONS

The Optik™ Incorporated advertisement "Babcock Endo–Grasper", Surgical Products, p. 33, Jun. 1992 edition.

*Primary Examiner*—Stephen C. Pellegrino
*Assistant Examiner*—William Lewis

[57] ABSTRACT

A multi-tool surgical apparatus is provided which includes a handle assembly, a body portion extending from the handle assembly and a plurality of different tool assemblies operatively associated with the body portion and actuable independent from one another each for performing a different surgical task during endoscopic or laparoscopic procedures. Preferably, a first surgical tool is operatively associated with a distal end of the body portion and a second surgical tool is operatively associated with a medial section of the body portion.

16 Claims, 8 Drawing Sheets

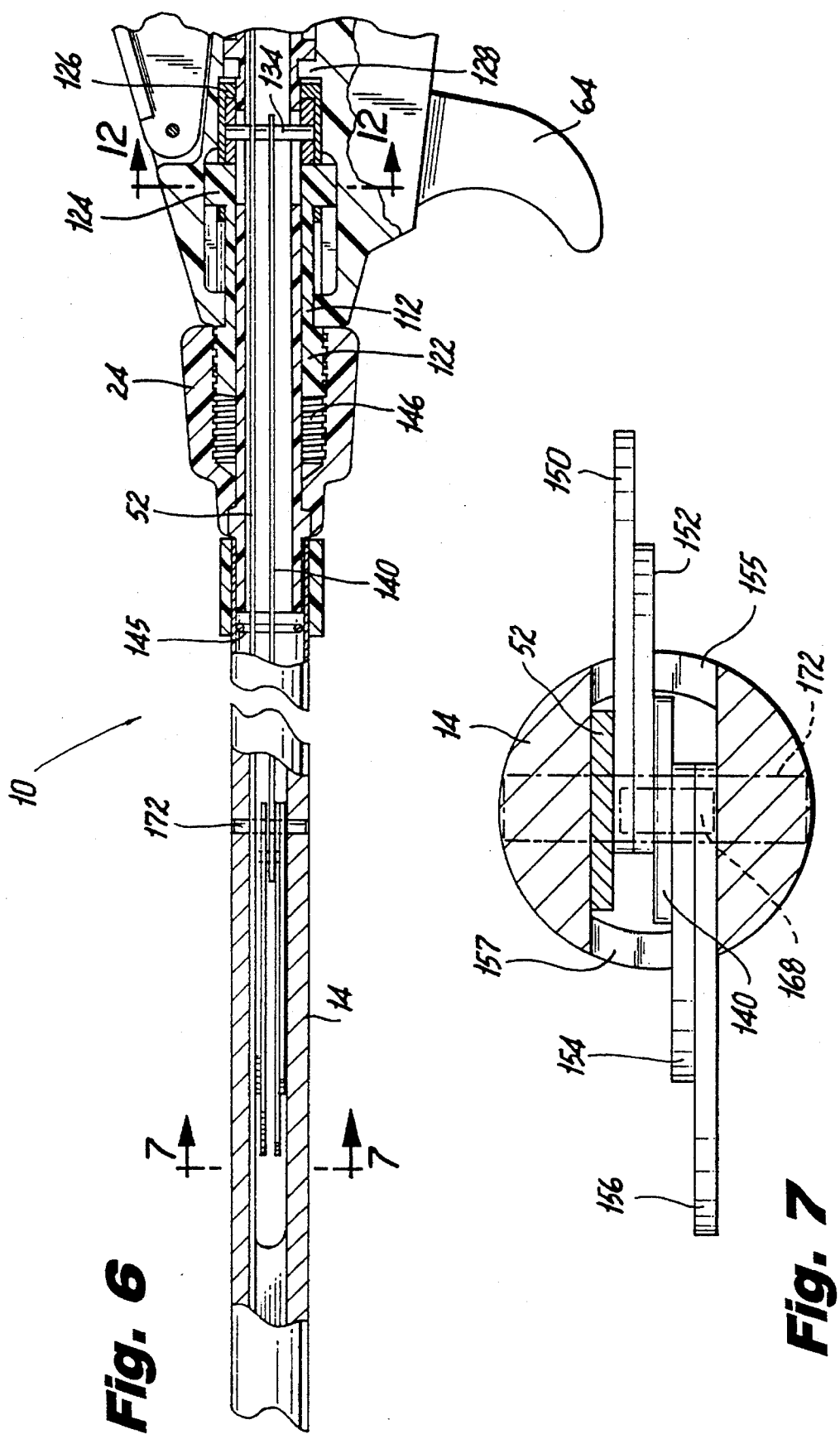

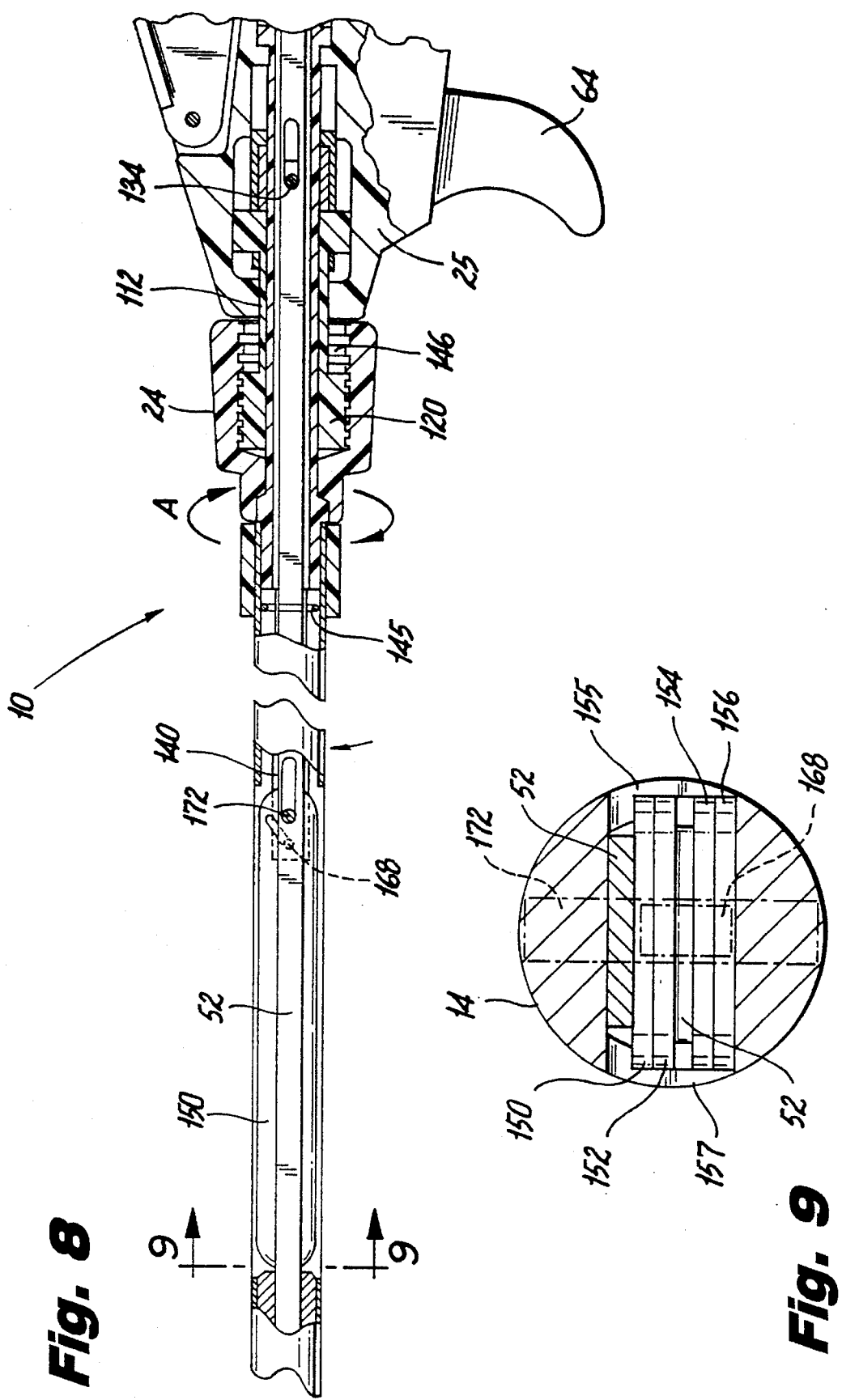

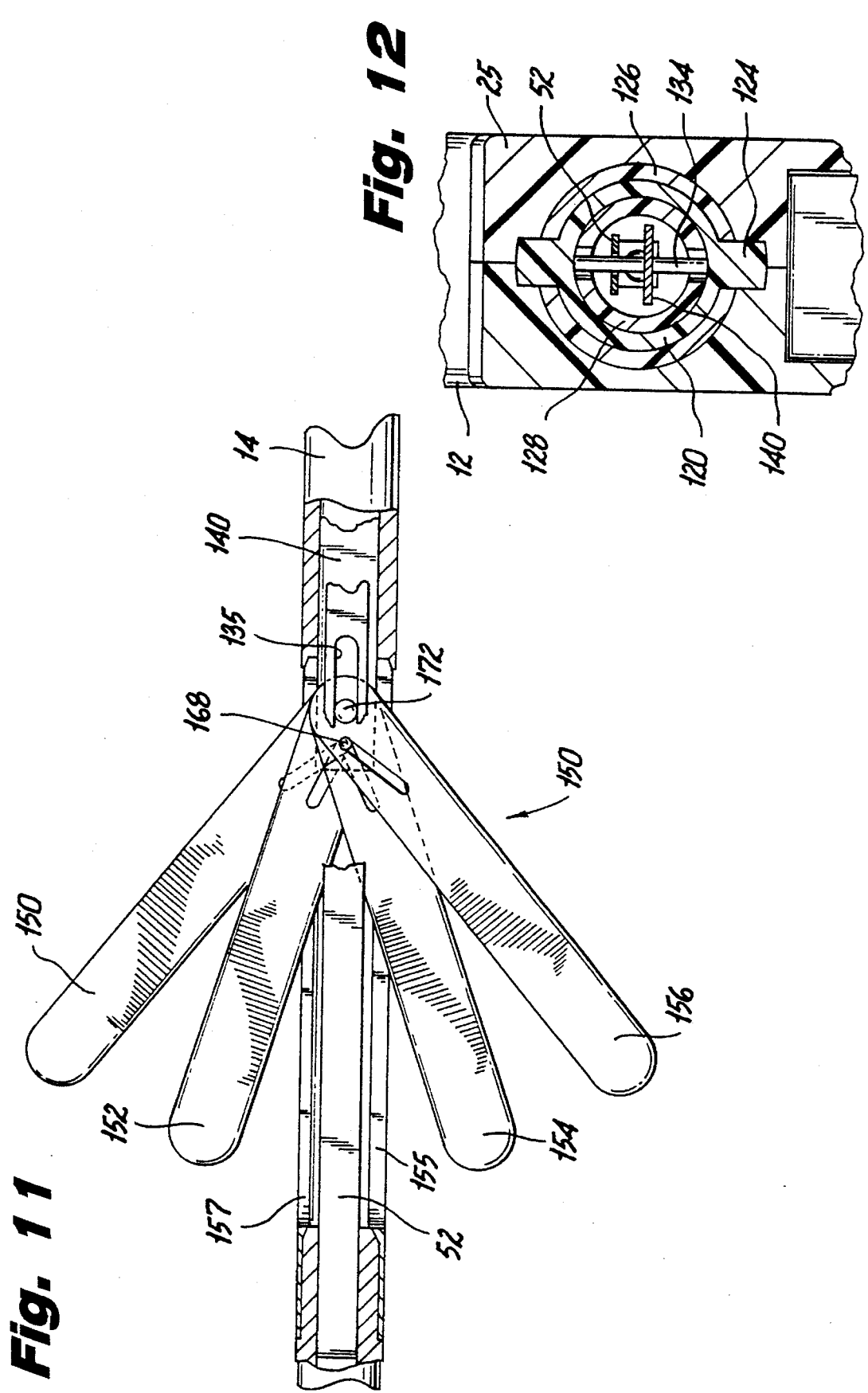

MULTI-TOOL SURGICAL APPARATUS

BACKGROUND OF THE INVENTION

1. Field of the Invention

This invention is directed to surgical instrumentation, ,and more particularly, to a unique surgical apparatus for performing a plurality of surgical tasks during endoscopic and/or laparoscopic surgical procedures.

2. Description of the Related Art

In laparoscopic and endoscopic surgical procedures, a small incision or puncture is made in the patient's body to provide access for a tube or cannula device. Once extended into the patient's body, the cannula allows insertion of various surgical instruments to perform the surgery.

Often, during an endoscopic procedure, it is necessary to perform a plurality of surgical tasks including, for example, retracting organs, grasping body tissue, or clamping blood vessels. In the past, whenever a particular surgical task was required during an endoscopic procedure, an instrument specifically suited for that particular task would be introduced to the surgical site through a cannula device. As a result, these procedures were often time consuming and necessarily required a plurality o surgical instruments, resulting in increased operating costs.

Recently, a laparoscopic surgical instrument having two pairs of independently actuable alligator jaws was disclosed in U.S. Pat. No. 5,147,373 to Ferzli. This instrument has a first pair of jaws at its distal end and a second pair of jaws disposed proximal of the first pair of jaws. Both jaw pairs are adapted to grasp and hold components such as sutures during a surgical procedure. This instrument, however, is limited in its ability to perform two different surgical tasks, such as, for example, retracting organs and grasping tissue.

It is desirable therefore, to provide a surgical apparatus for use in an endoscopic or laparoscopic surgical procedure which is equipped with a plurality of independently actuable surgical tools, each of which is particularly suited to perform a different surgical task.

SUMMARY OF THE INVENTION

A multi-tool surgical apparatus is provided which includes a handle assembly and a body portion which extends from the handle assembly and defines a longitudinal axis. First tool means are operatively associated with a distal end portion of the body portion for performing a first surgical task, and second tool means different from the first tool means are operatively associated with a medial section of the body portion for performing a second surgical task. First control means are provided for actuating the first tool means, and second control means are provided for actuating the second tool means.

The multi-tool surgical apparatus further includes rotation control means for rotating the body portion about the longitudinal axis thereof relative to the handle assembly. Means are also provided for locking the rotation control means in a desired angular position with respect to the handle assembly.

Preferably, the first tool means is a pair of cooperating jaw members which are movable between an open position and a closed position for performing such tasks as grasping or dissecting during a surgical procedure. Means are also provided for selectively maintaining the jaw members in a desired position. The second tool means is a plurality of interleaved cooperating blade members which are movable between an open position and a closed position for performing retraction tasks during a surgical procedure. It will be readily apparent to those skilled in the art that other tools can be substituted for either the first or second tool means including, for example, forceps, scissors, cautery tips, etc. and the tools can be arranged in any desired location.

In a preferred embodiment of the multi-tool surgical apparatus of the subject invention, the first control means is a pivoting actuation handle and a reciprocating control shaft operatively connected to the pivoting handle which extends through the body portion to the first tool means. The second control means preferably is an axial drive screw assembly which includes a progressively advanceable drive screw and a control rod which extends from the drive screw through the body portion to the second tool means.

Further features of the multi-tool surgical apparatus of the subject invention will become more readily apparent from the following detailed description of the invention taken in conjunction with the drawings.

BRIEF DESCRIPTION OF THE DRAWINGS

So that one skilled in the art to which the subject invention appertains will better understand how to make and use the invention, preferred embodiments of the multi-tool surgical apparatus will be described hereinbelow with reference to the drawings wherein:

FIG. 6 is a side elevational view in cross-section of the endoscopic portion of the instrument of FIG. 1 with the medial tool assembly thereof in an open position;

FIG. 7 is a cross-sectional view taken along line 7—7 of FIG. 6;

FIG. 8 is a side elevational view in cross-section of the endoscopic portion of the multi-tool surgical apparatus of FIG. 1, with the medial tool assembly thereof in a closed position, and rotated 90° from the position shown in FIG. 6;

FIG. 9 is a cross-sectional view taken along line 9—9 of FIG. 8;

FIG. 11 is a top plan view in cross-section of the endoscopic portion of the multi-tool surgical apparatus of FIG. 1, with the medial tool assembly thereof in an open position; and FIG. 12 is a cross-sectional view taken along line 12—12 of FIG. 6.

DETAILED DESCRIPTION OF THE PREFERRED EMBODIMENT

The present invention shall be discussed in terms of endoscopic procedures and apparatus. However, use herein of terms such as "endoscopic", "endoscopically", and "endoscopic portion", among others, should not be construed to limit the present invention to an apparatus for use only in conjunction with an endoscopic tube. To the contrary, it is believed that the present invention may find use in procedures wherein access is limited to a small incision including but not limited to arthroscopic and/or laparoscopic procedures.

Figure 1:
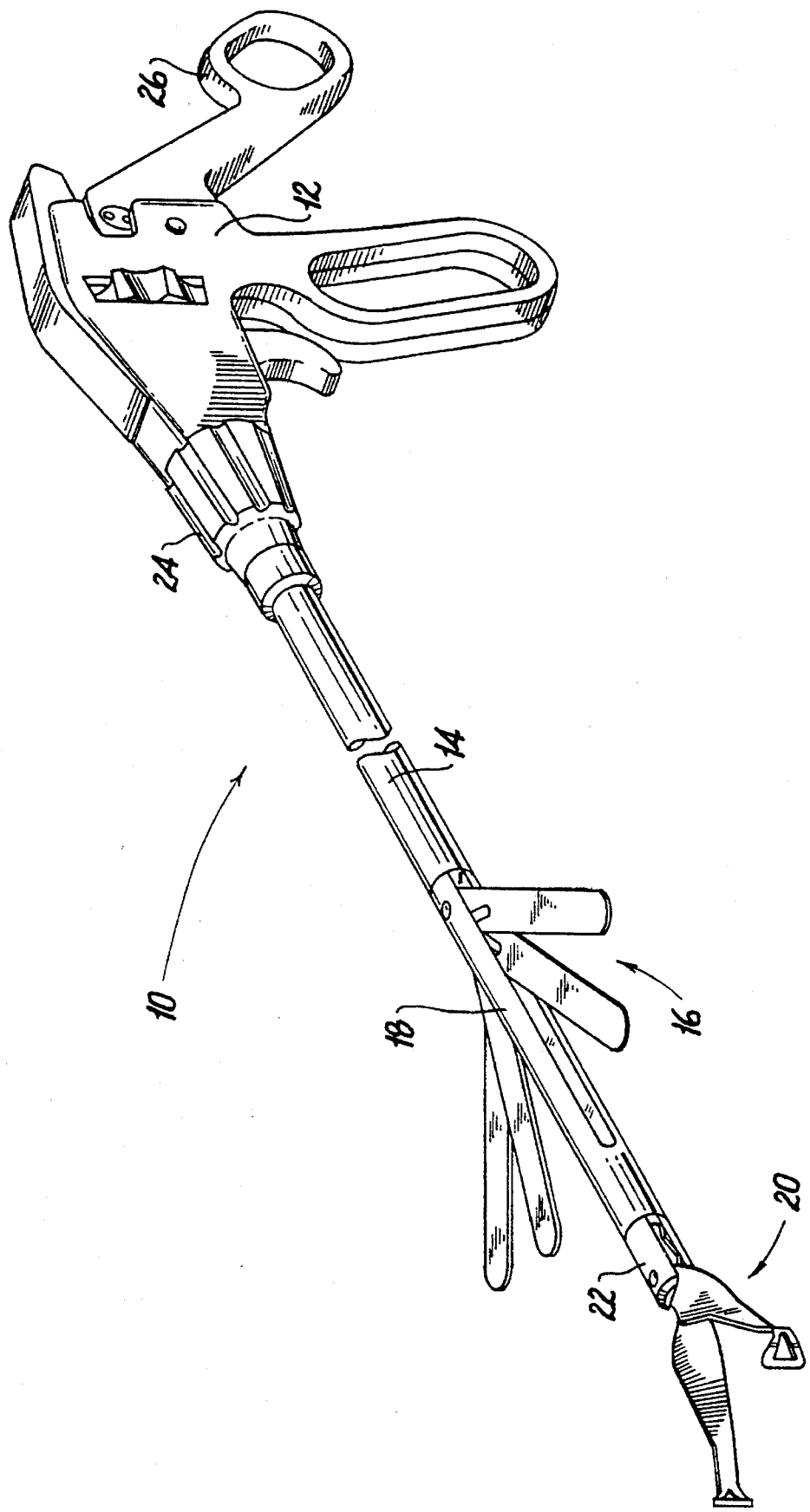
FIG. 1 is a perspective view of a multi-tool surgical apparatus in accordance with a preferred embodiment of the subject invention.

A multi-tool surgical apparatus in accordance with a preferred embodiment of the subject invention is illustrated in FIG. 1 and is designated generally by reference numeral 10. In brief, surgical apparatus 10 comprises a handle assembly 12 from which extends an elongated endoscopic body portion 14 defining a longitudinal axis. A first tool assembly 16 is associated with a medial section 18 of endoscopic portion 14 for performing a first surgical task, and a second tool assembly 20 is associated with a distal section 22 of endoscopic portion 14 for performing a second surgical task distinct from the first. The tool assemblies are independently actuable from handle assembly 12, and in particular, the first tool assembly 16 is actuable through rotation of collar 24, while the second tool assembly 20 is actuable through manipulation of pivoting handle 26. In the preferred embodiment described hereinbelow, the first tool assembly 16 will be characterized as a retractor assembly for manipulating body tissue and the second tool assembly 20 will be characterized as a grasping tool for engaging body tissue. However, those skilled in the art to which the subject invention appertains will readily appreciate that various other surgical tools can be incorporated into the subject invention. For example, the distal-most tool assembly could be configured in the form of scissors for cutting tissue or forceps for taking a biopsy of tissue.

Figure 2:
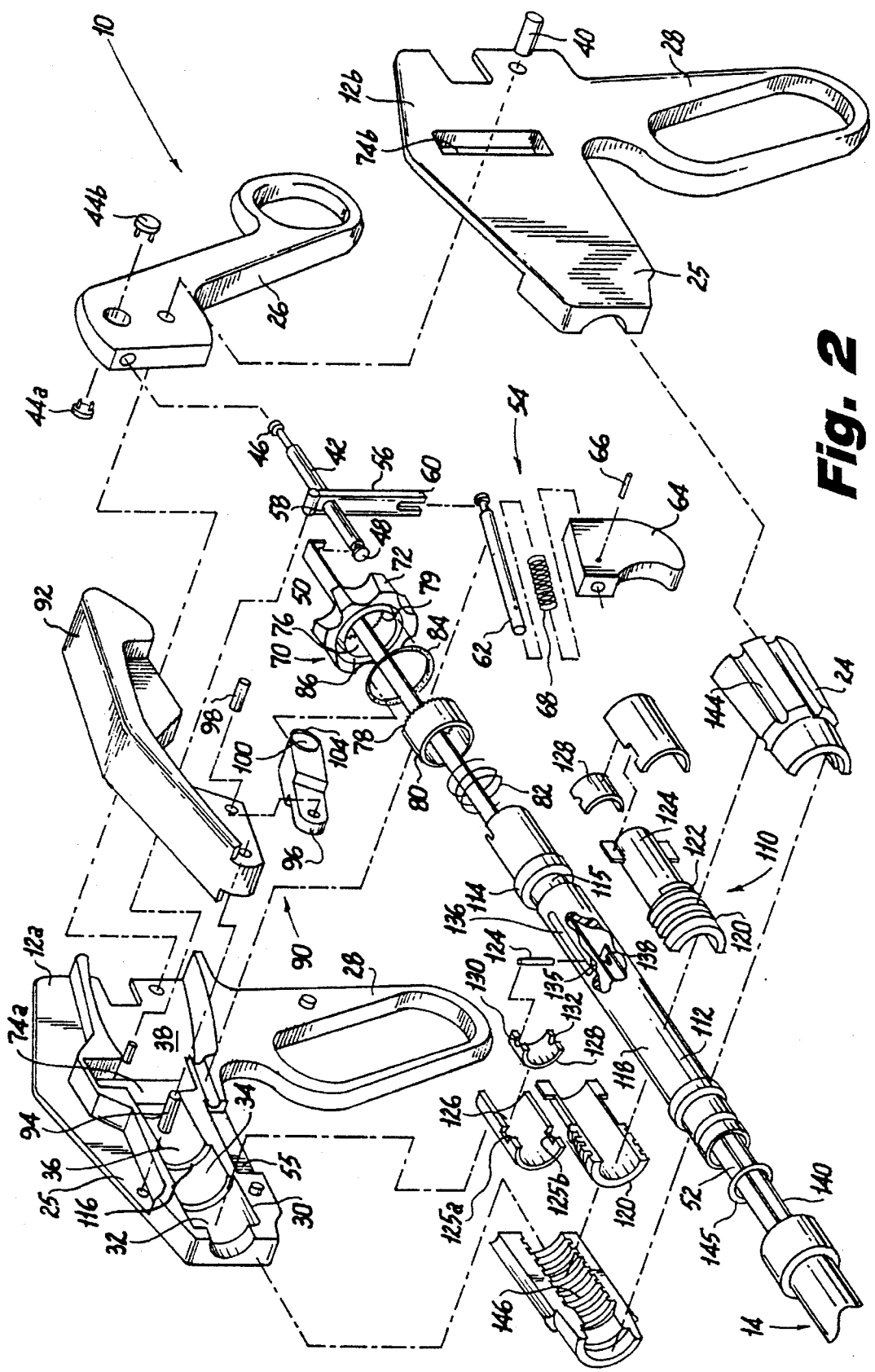
FIG. 2 is an exploded perspective view of the handle assembly of the multi-tool surgical apparatus of FIG.

Turning now to FIG. 2, the handle assembly 12 of the surgical apparatus 10 of the subject invention is constructed of two hemi-portions 12a and 12b which are fabricated from a lightweight plastic material, such as, for example, LEX brand material which is manufactured by the General Electric Corporation. Hemi-portions 12a and 12b are assembled together by known methods such as by adhesives, welding, pins, screws, etc. Once assembled, the handle hemi-portions 12a and 12b define an elongated barrel section 25 and a fixed gripping handle 28 depending from the barrel section 25. A stepped axial bore 30 is formed within barrel section 25 which defines a distal region 32, a medial region 34, and a proximal region 36, each region being dimensioned and configured to house a particular component of surgical instrument 10. A cavity 38 is also defined in barrel section 25, proximal to axial bore 30, for housing pivoting actuation handle 26. Actuation handle 26 pivots about pin member 40 and is operatively connected to the distal tool assembly 20 through a pair of cooperative transmission members. In particular, a transmission rod 42 is operatively connected to actuation handle 26 by two-part universal coupling 44a and 44b. The coupling permits rotational translation of handle 26 relative to the proximal end 46 of transmission rod 42 during operation. The distal end 48 of transmission rod 42 is coupled to the proximal end 50 of an elongated transmission bar 52. Transmission bar 52 extends from the handle assembly 12 of surgical apparatus 10, through the endoscopic portion 14 thereof, to the distal tool assembly 20 for effectuating its actuation.

Figure 3:
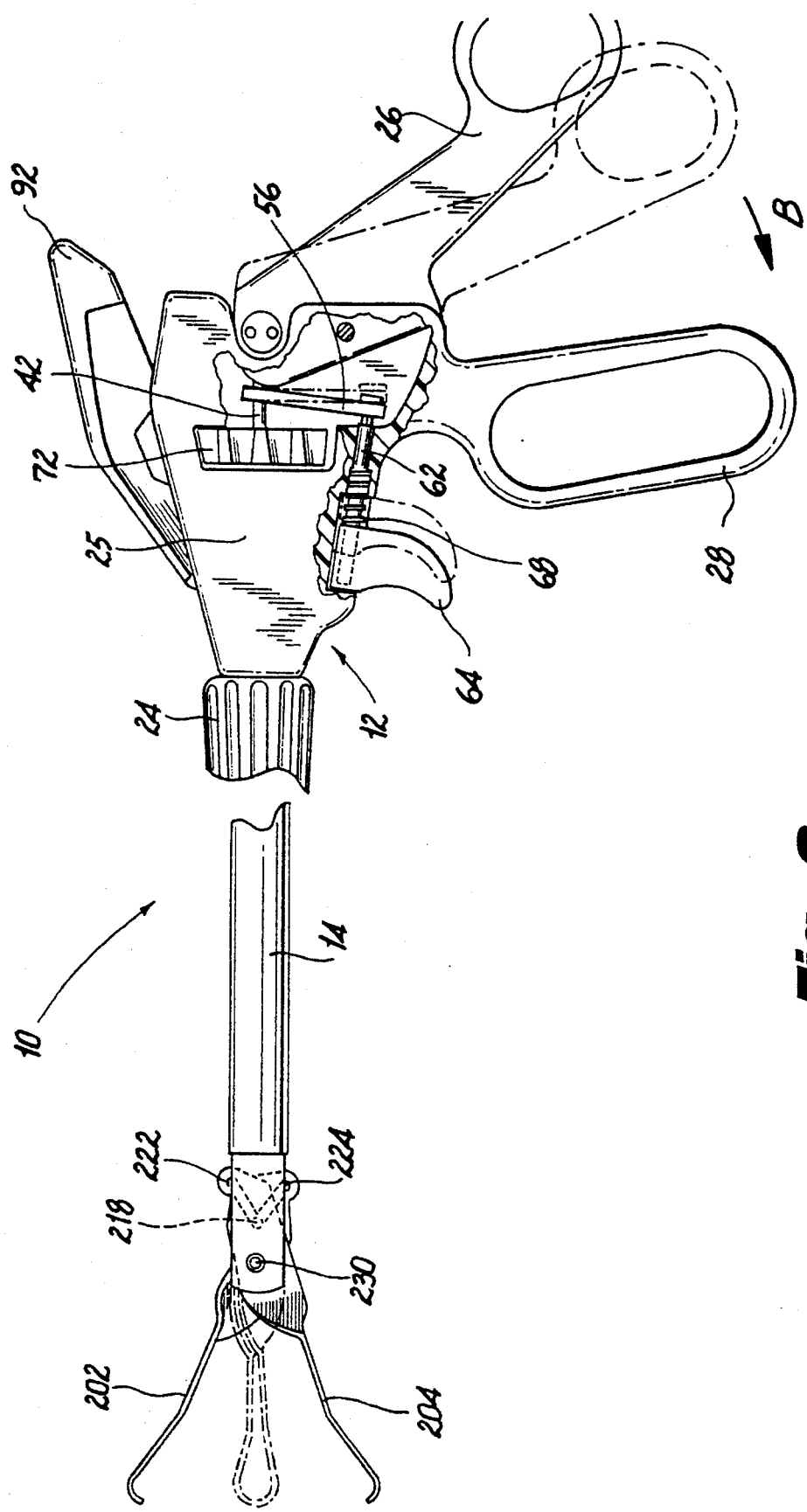
FIG. 3 is a side elevational view of the multi-tool surgical apparatus of FIG. 1, illustrating the operation of the distal tool assembly thereof.

A clutch assembly, indicated generally by reference numeral 54, is provided in association with transmission rod 48 and is positioned within a recess area 55 defined in barrel section 25 for controlling the longitudinal movement thereof. The clutch assembly includes a clutch member 56 mounted on a pivot post 57 and having an aperture 58 through which transmission rod 48 extends. A forked portion 60 is provided on clutch member 56 for engaging a push rod 62. Push rod 62 is connected to a trigger 64 by means of a pin 66. A coiled spring 68 is provided to bias trigger 64 in a distal direction to maintain clutch member 56 in an angled locking position, wherein the periphery of aperture 58 engages the circumference of transmission rod 48 maintaining it in a particular longitudinal position. As illustrated in FIG. 3, depression of trigger 64 against the bias of spring 68, will pivot clutch member 56 in a counter-clockwise direction, releasing transmission rod 42 and permitting handle 26 to pivotably return to an unactuated position.

Turning again to FIG. 2, the barrel section 25 of handle assembly 12 also houses a mechanism for effectuating the rotation of the endoscopic body portion 14 about the longitudinal axis thereof relative to handle assembly 12. This rotation effectuation mechanism is designated generally by reference numeral 70 and is operated by rotation of an annular dial member 72 accessible to the user through rectangular ports 74a and 74b defined in barrel section 25. An axial bore 76 is formed in dial member 72 for rotatably engaging a stationary bushing 78 maintained within the proximal region 32 of axial bore 30. More particularly, a toothed race 79 is formed in axial bore 76 to cooperate with a toothed race 80 formed on bushing 78. The cooperating teeth, which are biased into engagement by a coiled compression spring 82, permit incremental rotation of dial member 72 relative to bushing 78.

Figure 4:
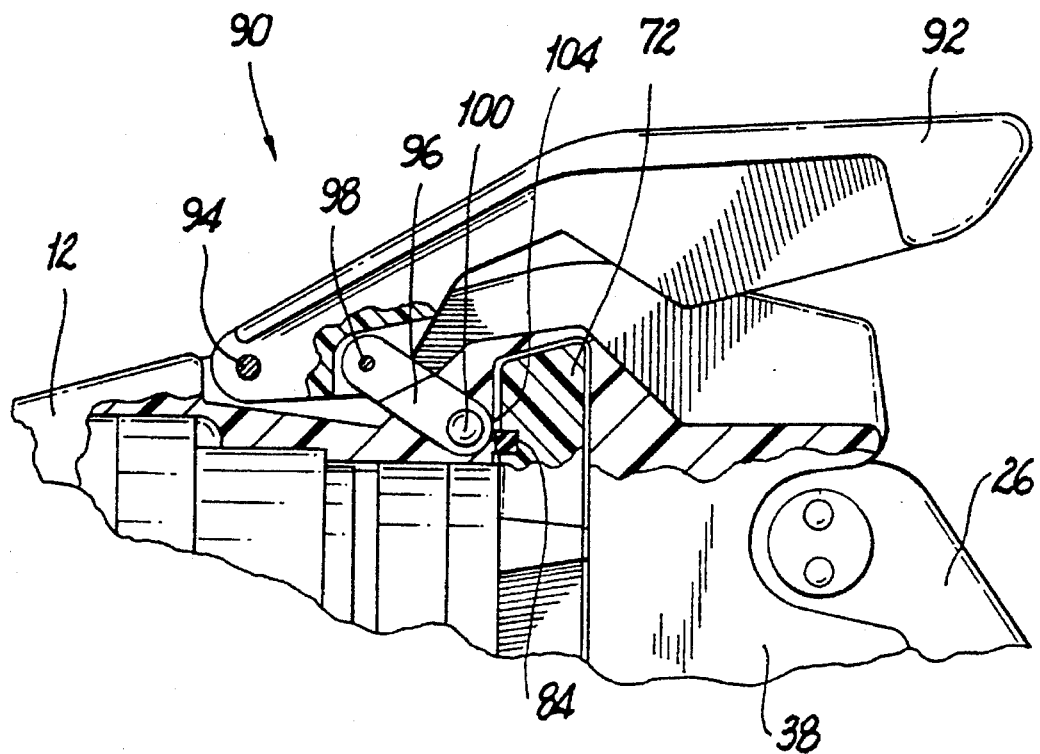
FIG. 4 is an elevational view of a locking mechanism associated with the multi-tool surgical apparatus of FIG. 1 in an unlocked position.
Figure 5:
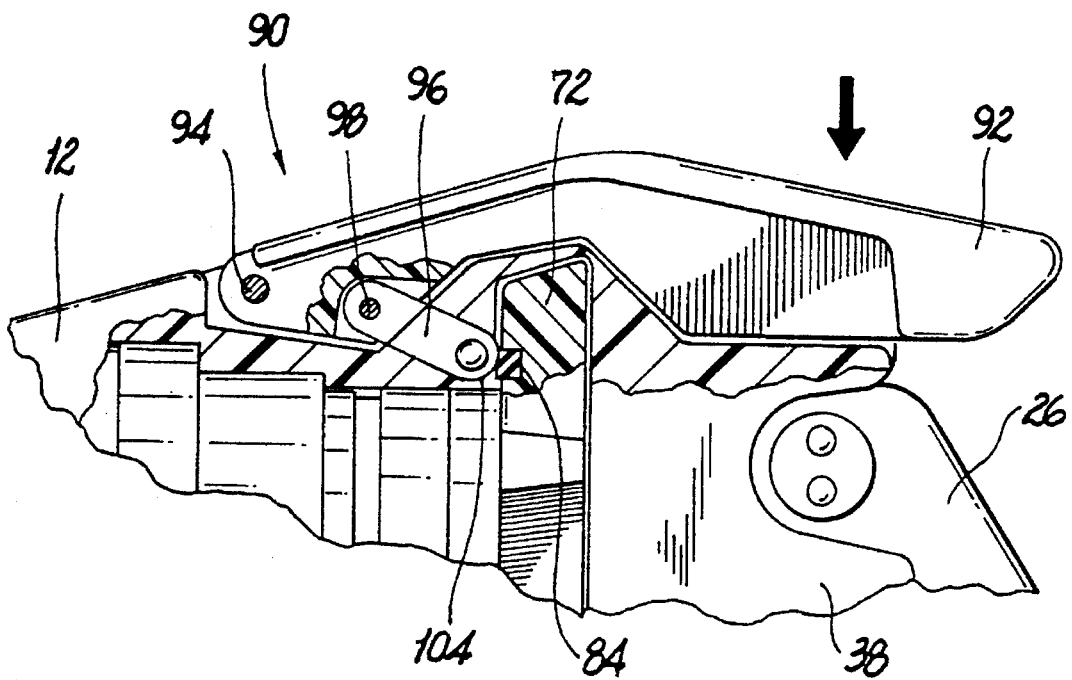
FIG. 5 is an elevational view of the locking mechanism of FIG. 4 in a locked position.

Preferably, an elastomeric ring 84 is disposed within an annular retention slot 86 formed in dial member 72. Ring 84 is selectively engagable by a frictional lock mechanism, designated generally by reference numeral 90, which is adapted to maintain dial member 72 in a desired rotated position. Lock mechanism 90 comprises a lever 92 pivotally mounted about post 94, and a rocker link 96 operatively mounted to lever 92 by a pivot pin 98 and pivotally mounted within barrel section 25 upon an integral pivot boss 100. The body portion of rocker link 96 defines an arcuate contact surface 104 dimensioned and configured to frictionally engage elastomeric ring 84. In use, locking mechanism 90 is selectively moved from the unlocked position of FIG. 4, wherein the arcuate surface 104 of rocker link 96 is out of contact with elastomeric ring 84 to the locked position of FIG. 5, wherein the arcuate surface 104 of rocker link 96 is in frictional contact with elastomeric ring 84. Once in frictional contact, rocker link 96 advantageously prevents the rotation of dial member 72, so as to maintain the endoscopic portion 14 of surgical apparatus 10 in a desired position or orientation.

Referring again to FIG. 2, taken in conjunction with FIG. 12, there is illustrated an axial drive screw assembly, designated generally by reference numeral 110, for actuating the medial tool assembly 16 of the subject invention. Drive screw assembly 110 is axially mounted about a guide tube 112 positioned substantially within the barrel section 25 of handle assembly 12. A circumferential flange 114 and an accompanying circumferential groove 115 are formed on guide tube 112, adjacent the proximal end thereof, for engaging circumferential rib 116 formed within the axial bore 30 of barrel section 25. An intermediate portion 118 of guide tube 112 extends distally through axial bore 30 and provides an axial path for the drive screw assembly 110. Drive screw assembly 110 includes a drive member 120 which defines a threaded portion 122 and a flanged portion 124. The flange portion 124 is dimensioned and configured to engage opposed ports 125a and 125b in retaining collar 126 to enable collar 126 to translate in conjunction with drive member 120. Collar 126 is dimensioned and configured to retain an annular bushing 128 which is provided with diametrically opposed apertures 130 and 132 for securing a thrust pin 134. Thrust pin 134 is engaged in an aperture 138 provided at the proximal end of a drive bar 140. Drive bar 140 extends from guide tube 112, through the endoscopic portion 14 of surgical apparatus 10, to the medial tool assembly 16 thereof to effectuate its operation. A longitudinal groove 136 is provided in guide tube 112 and a corresponding longitudinal groove 135 is provided in transmission bar 52 for enabling unobstructed translation of thrust pin 134 during operation of the apparatus 10. The drive screw assembly 110 further includes manipulation collar 24 which has a knurled external surface 144 and an internal threaded bore 146 for operatively engaging the threaded portion 122 of drive member 112 to effect axial translation thereof. Moreover, rotation of manipulation collar 24 will cause corresponding axial translation of drive member 112 relative to the longitudinal axis of endoscopic portion 14. For example, as best seen in FIGS. 6 and 8, rotation of collar 24 will cause axial advancement of drive member 112 from the proximal-most position of FIG. 6, to the distal-most position of FIG. 8. As a result, the thrust pin 134, maintained by bushing 128 and carried within collar 126, will urge drive bar 140 distally to actuate the medial tool assembly 16.

Referring to FIGS. 2, 6, and 8, a gaseous seal in the form of an elastomeric ring 145 is disposed within endoscopic portion 14 adjacent the axial drive screw assembly 110. The sealing ring 145 is provided to inhibit the egress of insufflation gases from the surgical site. In addition to the seal ring 145, silicone grease may be provided throughout the endoscopic portion 14 to further inhibit the egress of insufflation gas therethrough.

Figure 10:
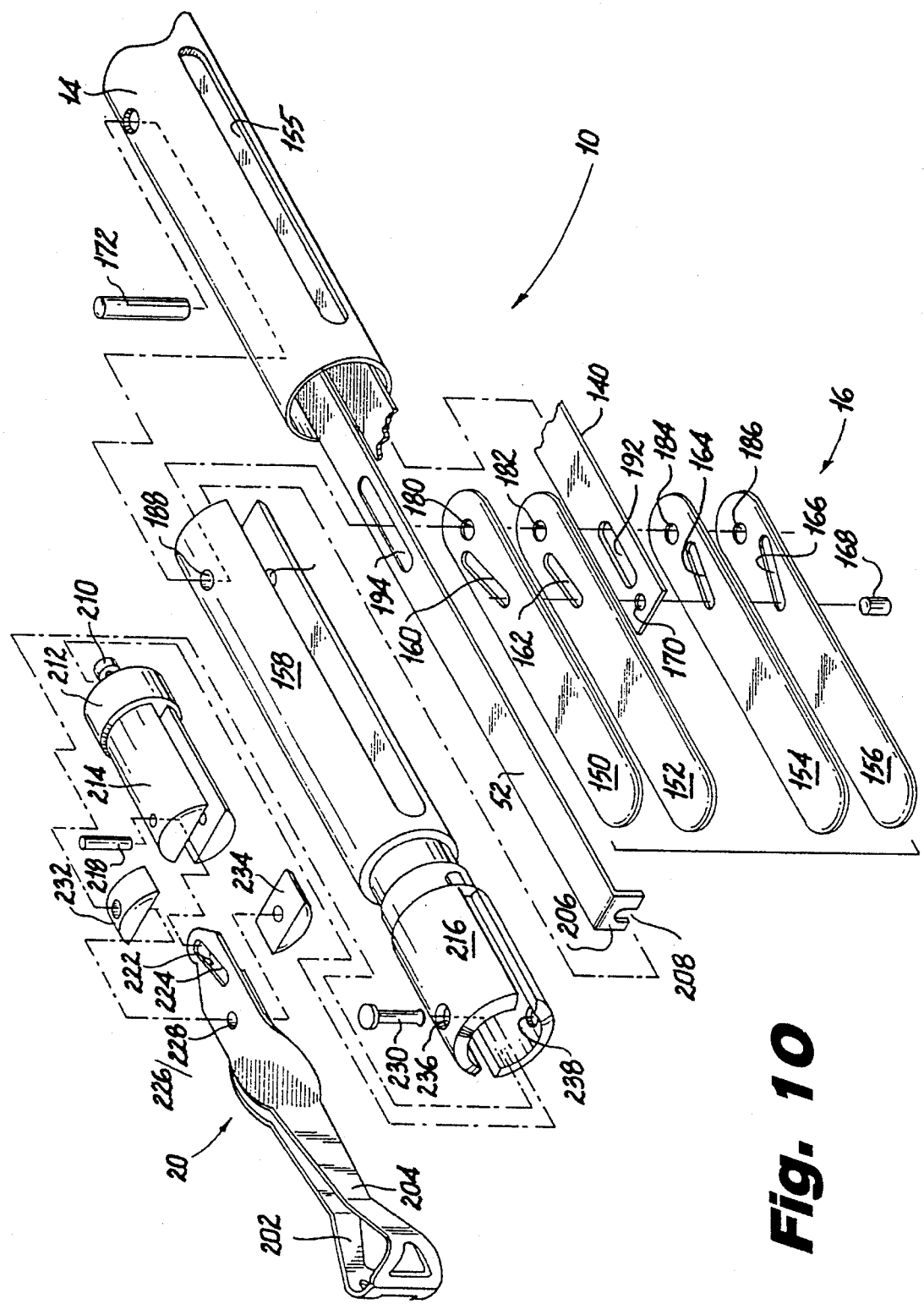
FIG. 10 is an exploded perspective view of the endoscopic portion and tool assembles of the multi-tool surgical apparatus of FIG. 1.

Referring to FIG. 10, taken in conjunction with FIGS. 3 and 11, the first and second tool assembly 16 and 20, respectively, are shown with parts separated for convenience of illustration. As discussed briefly hereinabove, the first tool assembly 16, which is associated with the medial section 18 of endoscopic portion 14, comprises a surgical retractor assembly for manipulating body tissue during a surgical procedure. The retractor assembly includes a plurality of cooperating interleaved blade members 150, 152, 154, and 156 pivotably mounted within a supporting yoke 158. A similar retractor assembly having a plurality of interleaved blades is described in commonly assigned U.S. Pat. No. 5,199,419 to Remiszewski et al., the disclosure of which is herein incorporated by reference. The retractor blades of the medial tool assembly 16 are configured to move between a closed position in alignment with the longitudinal axis of endoscopic body portion 14, as shown for example in FIG. 9, and an open position wherein the interleaved retractor blades are disposed in a symmetric fan-like configuration which is best seen in FIGS. 7 and 11. Opposed lateral slots 155 and 157 are defined in the medial section 18 of endoscopic body portion 14 to accommodate the fan-like deployment of the blades from an undeployed position enclosed within the endoscopic body portion 14. When the blades are in an undeployed position, body portion 14 is easily extended through a trocar or cannula device to introduce the instrument to the surgical site.

Referring to FIG. 11, the fan-like deployment of blade members 150–156 is achieved by providing each of the blades with an angularly disposed cam slot 160–166, respectively, within which a cam pin 168 translates. Cam pin 168 is mounted in an aperture 170 provided at the distal end of drive bar 140, the proximal end of which is associated with the drive screw assembly 110 described hereinabove. Blade members 150–156 are pivotably connected to one another through a pivot pin 172 which extends through pivot aperture 180–186 respectively formed in each of the blade members 150–156, and which is securely mounted in opposed apertures 188 and 190 provided in support yoke 158. A longitudinal groove 192 is defined in drive bar 140 proximal to aperture 170 to prevent movement of drive bar 140 relative to pivot pin 172. A corresponding longitudinal groove 194 is also provided in the proximal portion of transmission bar 52 which, as described hereinabove, extends to the distal tool assembly 20 to effectuate the actuation thereof.

The distal tool assembly 20, as described briefly hereinabove, comprises a pair of cooperative grasping jaws 202 and 204. Preferably, the grasping jaws are of the type known in the art as Babcock jaws, and are illustrated in FIG. 10. Another endoscopic surgical apparatus having grasping jaws of this type is described, for example, in commonly assigned U.S. patent application Ser. No. 07/781,069 filed Oct. 18, 1991, the disclosure of which is herein incorporated by reference. Other jaw configurations are also envisioned including, for example, Mixter jaws. The grasping jaws 202 and 204 of tool assembly 20 are movable between an open position and a closed position, as illustrated in FIG. 3, through the manipulation of actuation handle 26 which is operatively connected to transmission bar 52. The distal end of transmission bar 52 is provided with a downturned engaging flange 206 having a notch 208 for engaging a post 210 which depends from the proximal end portion 212 of jaw yoke 214. Jaw yoke 214 is operatively mounted within the distal portion 216 of support yoke 158. A cam pin 218 is associated with jaw yoke 214 for translating with respect to a pair of symmetrically disposed cam slots 222 and 224 provided in jaw members 202 and 204, respectively, to move the jaws between an open position and a closed position. Pivot apertures 226 and 228 extend through the shanks of jaw members 202 and 204, respectively, for accommodating a pivot pin 230. Pivot pin 230 also extends through a pair of arcuately shaped spacers 232 and 234 and is mounted within a pair of diametrically opposed apertures 236 and 238 which are provided in the distal portion of support yoke 158.

In operation, once introduced to the surgical site, the multi-tool surgical apparatus 10 of the subject invention can be employed to perform a plurality of surgical tasks. For example, to retract body tissue, the user may deploy the medial tool assembly 16 by rotating the manipulator collar 24 in the direction indicated by arrow "A" in FIG. 8. Rotation of collar 24 in this manner will cause drive member 112 to translate in a proximal direction, drawing therewith drive bar 140. Consequently, cam pin 168 is urged proximally, causing the blade members 150–156 to deploy in a fan-like manner as illustrated in FIG. 11. Once deployed, the retractor blades 150–156 provide a substantially planar tissue manipulation surface suitable for moving body tissue and large organs within the abdominal cavity of a patient.

When it is necessary to grasp tissue during a surgical procedure, the user may actuate the grasping jaws 202 and 204 of the distal tool assembly 20 by manipulating handle member 26. For example, to move the grasping jaws 202 and 204 from an open position to a closed position, handle 26 is pivoted in the direction indicated by arrow "B" in FIG. 3, so as to draw transmission bar 52 in a proximal direction. As a consequence, cam pin 218 is urged proximally, causing jaw members 202 and 204 to be cammed into a closed position, so as to grasp tissue therebetween. Concomitantly, the clutch member 56 of clutch assembly 54 operates to automatically engage and maintain the transmission rod 48 in a fixed longitudinal position, advantageously locking the grasping jaws 202 and 204 in a closed position. When the tissue is to be released from the grasping jaws 202 and 204, the user may depress trigger 64, causing push rod 62 to disengage clutch member 56 from transmission rod 48 and thereby permitting transmission bar 52 to translate in a distal direction to move the jaws 202 and 204 into an open position.

Although the multi-tool surgical apparatus of the subject invention has been described with respect to a preferred embodiment, it is apparent that changes or modifications may be made thereto without departing from the spirit or scope of the invention as defined by the appended claims.

What is claimed is:

1. A multi-tool surgical apparatus comprising:
   a) a handle assembly;
   b) a body portion extending from said handle assembly and defining a longitudinal axis;
   c) first tool means operatively associated with a distal end portion of said body portion for performing a first surgical task;
   d) second tool means different from said first tool means associated with said body portion and disposed proximal of said first tool means for performing a second surgical task;
   e) first control means for actuating said first tool means; and
   f) second control means for actuating said second tool means, at least one of said first and second control means disposed in axial alignment with said body portion, said second control means comprises an axial drive screw assembly including a progressively advanceable drive screw and a control rod, said rod extending from said drive screw through said body portion to said second tool means.

2. A multi-tool surgical apparatus as recited in claim 1, further comprising rotation control means for rotating said body portion about the longitudinal axis thereof relative to said handle assembly.

3. A multi-tool surgical apparatus as recited in claim 2, further comprising means for selectively locking said rotation control means in a desired angular position.

4. A multi-tool surgical apparatus as recited in claim 1, wherein said first tool means comprises a pair of cooperating jaw members movable between an open position and a closed position.

5. A multi-tool surgical apparatus as recited in claim 4, further comprising means for selectively maintaining said jaw members in a desired position.

6. A multi-tool surgical apparatus as recited in claim 1, wherein said second tool means comprises a plurality of interleaved cooperating blade members movable between an open position and a closed position.

7. A multi-tool surgical apparatus as recited in claim 1, wherein said first control means comprises a pivoting actuation handle and a reciprocating control shaft operatively connected to said pivoting handle, said shaft extending through said body portion to said first tool means.

8. A multi-tool surgical apparatus as recited in claim 1, wherein said body portion extending from said handle assembly is tubular in configuration.

9. A multi-tool surgical apparatus comprising:
   a) a handle assembly;
   b) a rotatable tubular body portion extending from said handle assembly and defining a longitudinal axis;
   c) rotation control means for rotating said tubular body portion about the longitudinal axis thereof relative to said handle assembly;
   d) locking means for selectively locking said rotation control means in a desired angular position;
   e) a pair of cooperating jaw members operatively associated with a distal end of said tubular body portion and movable between an open position and a closed position for performing a first surgical task;
   f) first actuation means for moving said jaw member between said open position and said closed position;
   g) a plurality of cooperating interleaved substantially planar blade members operatively associated with a medial section of said tubular body portion and movable between an open position and a closed position for performing a second surgical task; and
   h) second actuation means for moving said interleaved blade members between said open position and said closed position.

10. A multi-tool surgical apparatus as recited in claim 9, wherein said first actuation means comprises a pivoting actuation handle and a reciprocating control shaft operatively connected to said pivoting handle, said shaft extending through said tubular body portion to said pair of cooperating jaw members.

11. A multi-tool surgical apparatus comprising:
   a) a handle assembly;
   b) a tubular body portion extending from said handle assembly and defining a longitudinal axis;
   c) a pair of cooperating jaw members operatively associated with a distal end of said tubular body portion and movable between an open position and a closed position for performing a first surgical task;
   d) first actuation means for moving said jaw members between said open position and said closed position;
   e) means for selectively maintaining said jaw members in a desired position;
   f) plurality of cooperating interleaved substantially planar blade members operatively associated with a medial section of said tubular body portion and movable between an open position and a closed position for performing a second surgical task; and
   g) second actuation means for moving said interleaved blade members between said open position and said closed position.

12. A multi-tool surgical apparatus as recited in claim 11, wherein said first actuation means comprises a pivoting actuation handle and a reciprocating control shaft operatively connected to said pivoting handle, said shaft extending through said tubular body portion to said pair of cooperating jaw members.

13. A multi-tool surgical apparatus comprising:
   a) a handle assembly;
   b) a tubular body portion extending from said handle assembly and defining a longitudinal axis;
   c) a pair of cooperating jaw members operatively associated with a distal end of said tubular body portion and movable between an open position and a closed position for performing a first surgical task;
   d) first actuation means for moving said jaw members between said open position and said closed position;
   e) a plurality of cooperating interleaved substantially planar blade members operatively associated with a medial section of said tubular body portion and movable between an open position and a closed position for performing a second surgical task; and f) second actuation mean for moving said interleaved blade members between said open position and said closed position, said second actuation means comprises an axial drive screw assembly including a progressively advanceable drive screw assembly including a progressively advanceable drive screw and a control arm extending from said drive screw through said tubular body portion to said plurality of interleaved cooperating substantially planar blade members.

14. A multi-tool surgical apparatus as recited in claim 13, wherein said first actuation means comprises a pivoting actuation handle and a reciprocating control shaft operatively connected to said pivoting handle, said shaft extending through said tubular body portion to said pair of cooperating jaw members.

15. A multi-tool surgical apparatus comprising:

a) a handle assembly;

b) a elongated rotatable body portion extending from said handle assembly and defining a longitudinal axis;

c) rotation control means for rotating said body portion about the longitudinal axis thereof relative to said handle assembly;

d) locking means for selectively locking said rotation control means in a desired angular position;

e) a first tool mechanism operatively associated with a distal end portion of said body portion, said first tool mechanism movable upon activation of said handle assembly;

f) a second tool mechanism disposed proximal of said first tool mechanism; and g) means positioned distally of said handle assembly in axial alignment with said body portion for moving said second tool mechanism.

16. A multi-tool surgical apparatus comprising:

a) a handle assembly;

b) a body portion extending distally from said handle assembly and defining a longitudinal axis;

c) first and second members operatively associated with a distal end of said body portion;

d) third and fourth members operatively associated with a proximal end of said body portion;

e) first control means associated with said handle assembly for moving both said first and second tool members between first and second portions;

f) second rotatable control means associated with said body portion for moving both said third and fourth tool members between first and second portions, said rotatable means comprises an axial drive screw assembly including a progressively advanceable drive screw and a control rod, said rod extending from said drive screw through said body portion to said second tool means.

* * * * *